United States Patent
Huang et al.

(10) Patent No.: US 11,258,100 B2
(45) Date of Patent: Feb. 22, 2022

(54) ELECTROLYTE COMPOSITION AND METAL-ION BATTERY EMPLOYING THE SAME

(71) Applicant: Industrial Technology Research Institute, Hsinchu (TW)

(72) Inventors: Hsiao-Wen Huang, Kaohsiung (TW); Chun-Tsung Hsu, Tainan (TW); Che-Wei Chang, Taichung (TW); Ping-I Pan, Tainan (TW); Chien-Chih Chiang, New Taipei (TW); Chang-Chung Yang, Taipei (TW)

(73) Assignee: INDUSTRIAL TECHNOLOGY RESEARCH INTITUTE, Hsinchu (TW)

( * ) Notice: Subject to any disclaimer, the term of this patent is extended or adjusted under 35 U.S.C. 154(b) by 284 days.

(21) Appl. No.: 16/654,920

(22) Filed: Oct. 16, 2019

(65) Prior Publication Data
US 2020/0168954 A1    May 28, 2020

Related U.S. Application Data

(60) Provisional application No. 62/771,716, filed on Nov. 27, 2018.

(30) Foreign Application Priority Data

Dec. 28, 2018    (TW) .................................. 107147656

(51) Int. Cl.
*H01M 10/0568*    (2010.01)
*H01M 10/0567*    (2010.01)
(Continued)

(52) U.S. Cl.
CPC ...... *H01M 10/0568* (2013.01); *C07D 233/58* (2013.01); *C07F 5/022* (2013.01);
(Continued)

(58) Field of Classification Search
CPC .......... H01M 10/054; H01M 10/0567; H01M 10/0568; H01M 2300/0025; H01M 4/661; H01M 4/663; H01M 4/72; H01M 4/80
See application file for complete search history.

(56) References Cited

U.S. PATENT DOCUMENTS

| | | |
|---|---|---|
| 5,096,789 A | 3/1992 | Melton et al. |
| 6,368,486 B1 | 4/2002 | Thompson et al. |

(Continued)

FOREIGN PATENT DOCUMENTS

| | | |
|---|---|---|
| CN | 1181077 C | 12/2004 |
| CN | 102138235 A | 7/2011 |

(Continued)

OTHER PUBLICATIONS

Chinese Office Action and Search Report for Chinese Application No. 201910237766.4. dated Nov. 4, 2020.

(Continued)

*Primary Examiner* — Carlos Barcena
(74) *Attorney, Agent, or Firm* — Birch, Stewart, Kolasch & Birch, LLP

(57) ABSTRACT

An electrolyte composition and a metal-ion battery employing the same are provided. The electrolyte composition includes a metal chloride, an imidazolium salt of Formula (I), an alkali halide, and an oxalate-containing borate Formula (I)

(Continued)

wherein $R^1$, $R^2$, and $R^3$ are independently $C_{1-8}$ alkyl, $C_{2-8}$ alkenyl, $C_{2-8}$ alkynyl, $C_{1-8}$ alkoxy, $C_{2-8}$ alkoxyalkyl, or $C_{1-8}$ fluoroalkyl; and $X^-$ is $F^-$, $Cl^-$, $Br^-$, or $I^-$. The metal chloride is aluminum chloride, iron chloride, zinc chloride, copper chloride, manganese chloride, chromium chloride, or a combination thereof.

20 Claims, 1 Drawing Sheet

(51) Int. Cl.
 *H01M 10/054* (2010.01)
 *C07F 5/02* (2006.01)
 *C07D 233/58* (2006.01)

(52) U.S. Cl.
 CPC ..... *H01M 10/054* (2013.01); *H01M 10/0567* (2013.01); *H01M 2300/0025* (2013.01)

(56) References Cited

U.S. PATENT DOCUMENTS

| | | | |
|---|---|---|---|
| 8,715,853 | B1 | 5/2014 | Vajo et al. |
| 9,391,329 | B2 | 7/2016 | Yoon et al. |
| 9,466,853 | B2 | 10/2016 | Brown et al. |
| 2005/0164082 | A1 | 7/2005 | Kishi et al. |
| 2014/0363746 | A1 | 12/2014 | He |
| 2016/0141726 | A1 | 5/2016 | Young et al. |
| 2017/0033397 | A1 | 2/2017 | Brown et al. |
| 2017/0338513 | A1 | 11/2017 | Chiang et al. |
| 2017/0338514 | A1 | 11/2017 | Chiang et al. |

FOREIGN PATENT DOCUMENTS

| | | |
|---|---|---|
| CN | 102195091 A | 9/2011 |
| CN | 102569886 A | 7/2012 |
| CN | 102903954 A | 1/2013 |
| CN | 103094610 A | 5/2013 |
| CN | 104600352 A | 5/2015 |
| CN | 104969401 A | 10/2015 |
| CN | 106471660 A | 3/2017 |
| CN | 10794271 A | 11/2017 |
| CN | 107394260 A | 11/2017 |
| CN | 107615556 A | 1/2018 |
| CN | 108140891 A | 6/2018 |
| CN | 108321394 A | 7/2018 |
| JP | 10-97869 A | 4/1998 |
| JP | 2000-82493 A | 3/2000 |
| JP | 2308-218384 A | 9/2008 |
| JP | 2011-171310 A | 9/2011 |
| KR | 10-2004-0006429 A | 1/2004 |

OTHER PUBLICATIONS

Karuppasamy et al., "An enhanced electrochemical and cycling properties of novel boronic Ionic liquid based ternary gel polymer electrolytes for rechargeable Li/LiCoO2 cells", Scientific Reports, vol. 7, Sep. 2017. pp. 1-11.
Renjie et al., "Applications of Ionic Liquids in Batteries", Progress in Chemistry, vol. 23, No. 2/3, Mar. 2011, pp. 366-373.
Office Action issued in Taiwanese Patent Application No. 107147656 dated Sep. 19, 2019.
Scordilis-Kelley et al., "Lithium and Sodium Standard Reduction Potentials in Ambient-Temperature Chloroaluminate Molten Salts", J. Electrochem. Soc., vol. 140, No. 6, pp. 1606-1611, Jun. 1993.
Chinese Office Action and Search Report for Chinese Application No. 201910237766.4, dated Sep. 13, 2021.
Chinese Notice of Allowance and Search Report for Chinese Application No. 201910237766.4, dated Jan. 6, 2022.

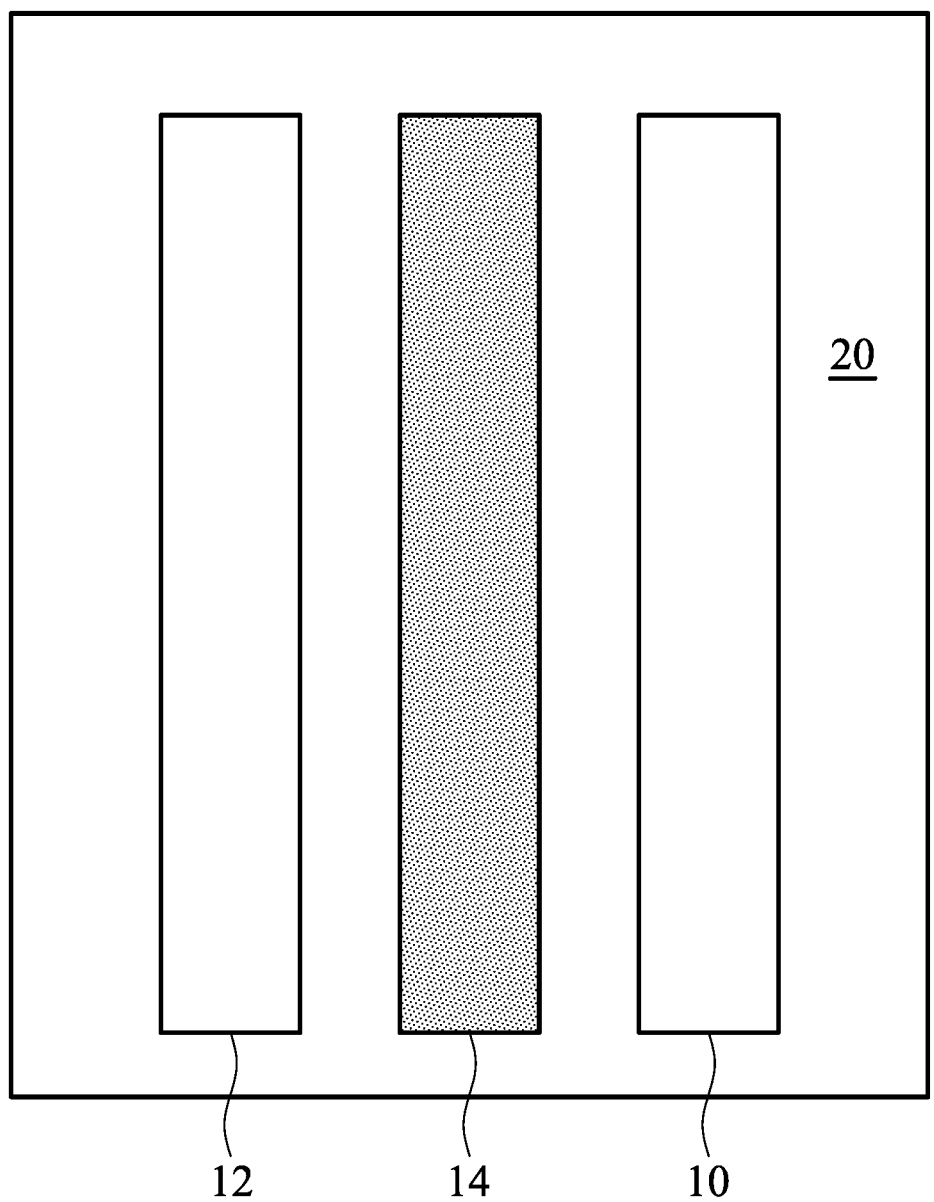

ELECTROLYTE COMPOSITION AND METAL-ION BATTERY EMPLOYING THE SAME

CROSS REFERENCE TO RELATED APPLICATIONS

This application claims the benefit of U.S. Provisional Application No. 62/771,716, filed on Nov. 27, 2018, which is hereby incorporated herein by reference.

The application is based on, and claims priority from, Taiwan Application Serial Number 107147656, filed on Dec. 28, 2018, the disclosure of which is hereby incorporated by reference herein in its entirety.

TECHNICAL FIELD

The disclosure relates to an electrolyte composition and a metal-ion battery employing the same.

BACKGROUND

Aluminum is the most abundant metal on earth, and electronic devices that are based on aluminum have the advantage of being inexpensive to produce. Furthermore, aluminum has low flammability and low electronic redox properties. This means that an aluminum-ion battery might offer significant safety improvements.

The electrolyte composition used in some conventional metal-ion batteries (such as an aluminum-ion battery) may include ionic liquid. For example, some aluminum-ion batteries employ an electrolyte composition including aluminum chloride and imidazolium chloride and exhibit good electrochemical reversibility. Due to the low operating voltage of the electrolyte composition, the power density and the application of the metal-ion batteries are limited. In addition, in the conventional electrolyte composition, the molar ratio of aluminum chloride to imidazolium chloride is not less than 1.3. As a result, excessive aluminum chloride is apt to react with water from the atmosphere, resulting in the decomposition of electrolyte. Therefore, the cycling stability of the metal-ion battery is reduced and the yield of the aluminum-ion battery employing the same is limited.

Therefore, the industry needs a novel electrolyte composition to overcome the problems mentioned above.

SUMMARY

According to embodiments of the disclosure, the disclosure provides an electrolyte composition. The electrolyte composition of the disclosure includes a metal chloride, an imidazolium salt having a structure represented by Formula (I), an alkali halide, and, an oxalate-containing borate

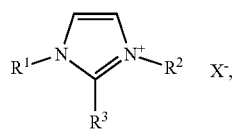

Formula (I)

wherein $R^1$, $R^2$ and $R^3$ can be independently $C_{1-8}$ alkyl group, $C_{2-8}$ alkenyl, $C_{2-8}$ alkynyl, $C_{1-8}$ alkoxy group, $C_{2-8}$ alkoxyalkyl, or $C_{1-8}$ fluoroalkyl; and, $X^-$ is $F^-$, $Cl^-$, $Br^-$, or $I^-$, the metal chloride is aluminum chloride, ferric chloride, zinc chloride, cupric chloride, manganese chloride, chromium chloride, or a combination thereof.

According to embodiments of the disclosure, the disclosure provides a metal-ion battery. The metal-ion battery can include a positive electrode, a separator, a negative electrode, and the aforementioned electrolyte composition, wherein the negative electrode and the positive electrode can be separated by the separator, and the electrolyte composition can be disposed between the positive electrode and the negative electrode.

A detailed description is given in the following embodiments with reference to the accompanying drawings.

BRIEF DESCRIPTION OF THE DRAWINGS

FIGURE is a schematic view of the metal-ion battery according to an embodiment of the disclosure.

DETAILED DESCRIPTION

The electrolyte composition and the metal-ion battery of the disclosure are described in detail in the following description. In the following detailed description, for purposes of explanation, numerous specific details and embodiments are set forth in order to provide a thorough understanding of the present disclosure. The specific elements and configurations described in the following detailed description are set forth in order to clearly describe the present disclosure. It will be apparent, however, that the exemplary embodiments set forth herein are used merely for the purpose of illustration, and the inventive concept may be embodied in various forms without being limited to those exemplary embodiments. In addition, the drawings of different embodiments may use like and/or corresponding numerals to denote like and/or corresponding elements in order to clearly describe the present disclosure. However, the use of like and/or corresponding numerals in the drawings of different embodiments does not suggest any correlation between different embodiments. In the drawings, the size, shape, or thickness of some of the elements may be exaggerated and not drawn on scale for illustrative purposes. The disclosure will be described with respect to particular embodiments and with reference to certain drawings but the disclosure is not limited thereto.

The disclosure provides an electrolyte composition and a metal-ion battery employing the same. According to embodiments of the disclosure, the electrolyte composition of the disclosure includes metal chloride and imidazolium salt having specific structure, wherein the molar ratio of metal chloride to imidazolium salt is controlled in a specific range. Besides metal chloride and imidazolium salt, the electrolyte composition of the disclosure further includes a specific amount of alkali halide and a specific amount of oxalate-containing borate. As a result, the electrolyte composition of the disclosure exhibits high conductivity, stability and redox reactivity, resulting in that the metal-ion battery, employing the electrolyte composition, can have high operating voltage (i.e. a discharging mean voltage of not less than 3.0V), high power density, high cycling stability, and prolonged lifespan.

According to embodiments of the disclosure, the electrolyte composition of the disclosure comprises a metal chloride, an imidazolium salt having a structure represented by Formula (I), an alkali halide, and an oxalate-containing borate,

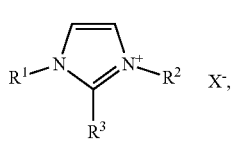

Formula (I)

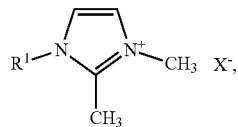

wherein $R^1$, $R^2$ and $R^3$ can be independently $C_{1-8}$ alkyl group, $C_{2-8}$ alkenyl, $C_{2-8}$ alkynyl, $C_{1-8}$ alkoxy group, $C_{2-8}$ alkoxyalkyl, or $C_{1-8}$ fluoroalkyl; and, $X^-$ is $F^-$, $Cl^-$, $Br^-$, or $I^-$.

According to embodiments of the disclosure, the metal chloride can be aluminum chloride, ferric chloride, zinc chloride, cupric chloride, manganese chloride, chromium chloride, or a combination thereof. Herein, the metal chloride of the disclosure can include at least one metal halide with various valences. For example, aluminum chloride of the disclosure can be $AlCl_2$, $AlCl_3$, or a combination thereof; copper chloride of the disclosure can be $CuCl$, $CuCl_2$, or a combination thereof; iron chloride can be $FeCl_2$, $FeCl_3$, or a combination thereof; chromium chloride can be $CrCl_2$, $CrCl_3$, or a combination thereof; zinc chloride can be $ZnCl_2$, $ZnCl_4$, or a combination thereof; and, manganese chloride can be $MnCl_2$, $MnCl_3$, or a combination thereof.

According to embodiments of the disclosure, $C_{1-8}$ alkyl group can be linear or branched alkyl group. For example, $C_{1-8}$ alkyl group can be methyl, ethyl, propyl, butyl, pentyl, hexyl, heptyl, octyl, or isomer thereof. According to embodiments of the disclosure, $C_{2-8}$ alkenyl can be linear or branched alkenyl. For example, $C_{2-8}$ alkenyl can be ethenyl, propenyl, butenyl, pentenyl, hexenyl, heptenyl, octenyl, or isomer thereof. According to embodiments of the disclosure, $C_{2-8}$ alkynyl can be linear or branched alkynyl. For example, $C_{2-8}$ alkynyl can be ethynyl, propynyl, butynyl, pentynyl, hexynyl, heptynyl, octynyl, or isomer thereof. According to embodiments of the disclosure, $C_{1-8}$ alkoxy group can be linear or branched alkoxy group. For example, $C_{1-8}$ alkoxy group can be methoxy, ethoxy, propoxy, butoxy, pentoxy, hexoxy, heptoxy, octoxy, or isomer thereof. According to embodiments of the disclosure, $C_{2-8}$ alkoxyalkyl can be linear or branched alkoxyalkyl. For example, $C_{2-8}$ alkoxyalkyl can be methoxymethyl, ethoxymethyl, methoxyethyl, propoxymethyl, or isomer thereof. According to embodiments of the disclosure, $C_{1-8}$ fluoroalkyl can be an alkyl group which a part of or all hydrogen atoms bonded on the carbon atom are replaced with fluorine atoms, and $C_{1-8}$ fluoroalkyl can be linear or branched fluoroalkyl, such as fluoromethyl, fluoroethyl, fluoropropyl, or isomer thereof. For example, fluoromethyl can be monofluoromethyl group, difluoromethyl group, or trifluoromethyl group. Fluoroethyl can be monofluoroethyl group, difluoroethyl group, trifluoroethyl group, tetrafluoroethyl, or perfluoroethyl.

According to embodiments of the disclosure, $R^1$, $R^2$ and $R^3$ can be independently methyl, ethyl, propyl, butyl, pentyl, hexyl, heptyl, octyl, or isomer thereof. According to embodiments of the disclosure, $R^1$, $R^2$ and $R^3$ can be independently ethenyl, propenyl, butenyl, pentenyl, hexenyl, heptenyl, octenyl, ethynyl, propynyl, butynyl, pentynyl, hexynyl, heptynyl, octynyl, methoxymethyl, ethoxymethyl, methoxyethyl, propoxymethyl, fluoromethyl, fluoroethyl, or fluoropropyl.

According to embodiments of the disclosure, the imidazolium salt having a structure represented by Formula (I) can be wherein $R^1$ and $X^-$ are the same as defined above. For example, the imidazolium salt of the disclosure can be 1,2-dimethyl-3-propylimidazolium chloride (DMPIC), 1,2-dimethyl-3-propylimidazolium iodide, 1,2-dimethyl-3-propylimidazolium bromide, 1,2-dimethyl-3-propylimidazolium fluoride, 1,2-dimethyl-3-butylimidazolium chloride (DMBIC), 1,2-dimethyl-3-butylimidazolium iodide, 1,2-dimethyl-3-butylimidazolium bromide, 1,2-dimethyl-3-butylimidazolium fluoride, 1,2-dimethyl-3-ethylimidazolium chloride (DMEIC), 1,2-dimethyl-3-ethylimidazolium iodide, 1,2-dimethyl-3-ethylimidazolium bromide, 1,2-dimethyl-3-ethylimidazolium fluoride, or a combination thereof.

According to embodiments of the disclosure, besides the imidazolium salt having the structure represented by Formula (I), the electrolyte composition of the disclosure does not include other imidazolium salt and ionic liquid, in order to prevent the conductivity, stability, and redox reactivity of the electrolyte composition from being deteriorated by other imidazolium salt and/or ionic liquid.

Herein, when replacing the imidazolium salt having the structure represented by Formula (I) with other imidazolium salt (such as 1-butyl-3-methylimidazolium chloride (BMIC) or 1-ethyl-3-methylimidazolium chloride (EMIC)), the metal-ion battery, employing the electrolyte composition, would exhibit longer low-voltage-plateau and shorter high-voltage-plateau, thereby reducing the operating voltage of the metal-ion battery. For example, when replacing 1,2-dimethyl-3-propylimidazolium chloride (DMPIC) with 1-butyl-3-methylimidazolium chloride (BMIC) or 1-ethyl-3-methylimidazolium chloride (EMIC), the obtained metal-ion battery would have a discharging mean voltage less than 2.5V.

According to embodiments of the disclosure, in the electrolyte composition of the disclosure, the molar ratio of the metal chloride to the imidazolium salt is from 1.05 to 1.2, such as 1.08, 1.1, 1.12, 1.15, or 1.18. When the molar ratio of the metal chloride to the imidazolium salt is too low, a Lewis basic electrolyte composition would be obtained. The electrolyte composition is not apt to form an eutectic system, resulting from that alkali halide would not be completely dissolved in a Lewis basic electrolyte composition. Thus, the obtained electrolyte composition exhibits low conductivity, stability, and redox reactivity. When the molar ratio of the metal chloride to the imidazolium salt is too high, a Lewis acidic electrolyte composition would be obtained. Thus, the obtained electrolyte composition exhibits low conductivity, stability, redox reactivity and limited potential window.

According to embodiments of the disclosure, the alkali halide of the disclosure can be lithium chloride, sodium chloride, potassium chloride, rubidium chloride, cesium chloride, lithium fluoride, sodium fluoride, potassium fluoride, rubidium fluoride, cesium fluoride, lithium fluoride, sodium bromide, potassium bromide, rubidium bromide, cesium bromide, lithium iodide, sodium iodide, potassium iodide, rubidium iodide, cesium iodide, or a combination thereof.

According to embodiments of the disclosure, the ratio of the weight of the alkali halide to the total weight of the metal chloride and the imidazolium salt can be from 1:100 to 6:100 or from 2:100 to 6:100, such as 2.5:100, 3:100, 4:100, 5:100, or 5.5:100. When the ratio of the weight of the alkali halide to the total weight of the metal chloride and the imidazolium salt is too low, a Lewis acidic electrolyte composition would be obtained. As a result, $Al_2C_7^-$ ion would be easily produced from the electrolyte composition during charging and discharging, resulting in that an aluminum layer is apt to be formed on the negative electrode. Thus, the operating voltage, power density, cycling stability, and life cycle of the metal-ion battery are reduced. When the ratio of the weight of the alkali halide to the total weight of the metal chloride and the imidazolium salt is too high, alkali halide would not be completely dissolved in a Lewis basic electrolyte composition to form an eutectic system. Thus, the obtained electrolyte composition exhibits low conductivity, stability, and redox reactivity.

According to embodiments of the disclosure, the oxalate-containing borate of the disclosure can be

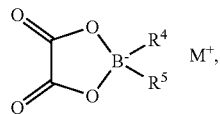

wherein $R^4$ and $R^5$ are halogen (such as fluorine, chlorine, bromine, or iodine); and, $M^+$ is $Li^+$ or $Na^+$. In addition, $R^4$ and $R^5$ can form an oxalate ligand

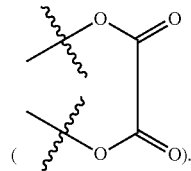

Therefore, the oxalate-containing borate of the disclosure can be

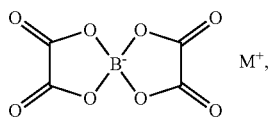

wherein $M^+$ is $Li^+$ or $Na^+$.

According to embodiments of the disclosure, the oxalate-containing borate of the disclosure is lithium bis(oxalato)borate (LiBOB), sodium bis(oxalato)borate (NaBOB), lithium difluoro(oxalato)borate (LiODFB), sodium difluoro(oxalato)borate (NaODFB), or a combination thereof. Since the electrolyte composition of the disclosure includes the oxalate-containing borate (such as lithium bis(oxalato)borate (LiBOB), or lithium difluoro(oxalato)borate (LiODFB)), the electrolyte composition can form a network (or dendritic) film, which is unable to be dissolved by ionic liquid (i.e. the imidazolium salt of the disclosure), during charging and discharging. Thus, the cycling stability and life cycle of the metal-ion battery is increased.

When replacing the oxalate-containing borate of the disclosure with other alkali metal salt (such as $LiPF_6$, $LiBF_4$, $LiClO_4$, $LiCF_3SO_3$, $LiAsF_6$, $LiSbF_6$, $LiAlCl_4$, $CH_3SO_3Li$, $CF_3SO_3Li$, lithium bis(fluorosulfonyl)imide (LiFSI), or lithium bis(trifluoromethylsulfonyl)imide (LiTFSI)), carbonic ester (such as ethylene carbonate (EC), vinylene carbonate (VC), or fluoroethylene carbonate (FEC)), or sulfur-containing compound (such as ethylene sulfite (ES), or benzenesulfonyl chloride), the film (which is formed from other alkali metal salt, carbonic ester, or sulfur-containing compound during charging and discharging) would be dissolved by ionic liquid. As a result, the network (or dendritic) film (which is unable to be dissolved by ionic liquid and is formed from the oxalate-containing borate of the disclosure during charging and discharging) cannot be prepared by means of other alkali metal salt, carbonic ester, or sulfur-containing compound. Therefore, the cycling stability and life cycle of the metal-ion battery would not be improved, when replacing the oxalate-containing borate of the disclosure with the other alkali metal salt, carbonic ester, or sulfur-containing compound.

According to embodiments of the disclosure, the ratio of the molar amount of the oxalate-containing borate to the total molar amount of the metal chloride and the imidazolium salt is from 0.1:100 to 2:100. According to embodiments of the disclosure, the ratio of the molar amount of the oxalate-containing borate to the total molar amount of the metal chloride and the imidazolium salt is not greater than 2:100, such as from 0.1:100 to 1.8:100. According to embodiments of the disclosure, the ratio of the molar amount of the oxalate-containing borate to the total molar amount of the metal chloride and the imidazolium salt can be 0.2:100, 0.5:100, 0.8:100, 1:100, 1.2:100, 1.5:100, or 1.75:100. When the ratio of the molar amount of the oxalate-containing borate to the total molar amount of the metal chloride and the imidazolium salt is too low, the network (or dendritic) film would not be formed during charging and discharging the metal-ion battery due to the insufficiency of oxalate-containing borate, resulting in that the cycling stability and life cycle of the metal-ion battery are not improved. When the ratio of the molar amount of the oxalate-containing borate to the total molar amount of the metal chloride and the imidazolium salt is too high, the power consumption of the metal-ion battery is increased, thereby reducing the power density of the metal-ion battery.

According to embodiments of the disclosure, the electrolyte composition of the disclosure can consists of said metal chloride, said imidazolium salt having the structure represented by Formula (I), said alkali halide, and said oxalate-containing borate. The amounts of components of the electrolyte composition of the disclosure are the same as defined above.

According to embodiments of the disclosure, the disclosure also provides a metal-ion battery. FIGURE is a schematic view of the metal-ion battery 100 according to an embodiment of the disclosure. The metal-ion battery 100 can include a positive electrode 10, a negative electrode 12, and an separator 14, wherein the separator 14 disposed between the positive electrode 10 and the negative electrode 12 to separate the negative electrode 12 and the positive electrode 10 from each other, preventing the positive electrode 10 from coming into direct contact with the negative electrode 12. The metal-ion battery 100 includes the aforementioned electrolyte composition 20 disposes in the metal-ion battery 100 and disposes between the positive electrode 10 and the negative electrode 12. Thus, the electrolyte composition 20 comes into contact with the positive electrode 10 and the negative electrode 12. The metal-ion battery can be a rechargeable secondary battery or it can be a primary battery.

According to embodiments of the disclosure, the positive electrode 10 can include a current-collecting layer of the positive electrode and an active material of the positive electrode disposed on the current-collecting layer of the positive electrode. According to embodiments of the disclosure, the positive electrode can consist of the current-collecting layer of the positive electrode and the active material of the positive electrode. According to embodiments of the disclosure, the current-collecting layer of the positive electrode can be a conductive carbon substrate, such as carbon cloth, carbon felt, or carbon paper. For example, the conductive carbon substrate can have a sheet resistance from about 1 $m\Omega \cdot cm^2$ to 6 $m\Omega \cdot cm^2$, and a carbon content of greater than 65 wt %. According to embodiments of the disclosure, the current-collecting layer of the positive electrode can be a metal material with porous structure, such as metal material having a three-dimensional network structure (such as nickel mesh, copper net, or molybdenum mesh) or metal material having a foam structure (such as nickel foam, copper foam, or molybdenum foam). According to embodiments of the disclosure, the metal material with porous structure can have a porosity P from about 50% to 80% (such as about 60%, or 70%). The porosity P can be determined by the following equation: $P=V1/V2\times 100\%$, wherein V1 is the volume of the pores of the current-collecting layer, and V2 is the volume of the current-collecting layer. According to embodiments of the disclosure, the current-collecting layer can be a composite layer of the conductive carbon substrate and a metal material.

According to embodiments of the disclosure, the active material of the positive electrode can be layered carbon material, layered double hydroxide, layered oxide, layered chalcogenide, vanadium oxide, metal sulfide, a combination thereof. According to embodiments of the disclosure, the layered carbon material can be graphite, carbon nanotube, graphene, or a combination thereof. According to embodiments of the disclosure, the layered carbon material can be intercalated carbon material, such as graphite (e.g., natural graphite, electrographite, pyrolytic graphite, foamed graphite, flake graphite, or expanded graphite), graphene, carbon nanotube or a combination thereof. According to embodiments of the disclosure, the active material of the positive electrode can grow directly on the current-collecting layer of the positive electrode (i.e. there is no other layer between the active layer and the current-collecting layer). For example, the active material can grow directly on the current-collecting layer by chemical vapor deposition (CVD). Furthermore, the active material of the positive electrode can be affixed to the current-collecting layer of the positive electrode via an adhesive. The adhesive can be polyvinyl alcohol (PVA), polytetrafluoroethylene (PTFE), carboxymethyl cellulose sodium, polyvinylidene difluoride (PVDF), styrene-butadiene copolymer, fluorinated rubber, polyurethane, polyvinylpyrrolidone, poly(ethyl acrylate), polyvinyl chloride, polyacrylonitrile, polybutadiene, polyacrylic acid, or a combination thereof. According to embodiments of the disclosure, when the current-collecting layer is metal material with porous structure, the active material of the positive electrode can further fill into the pores of the metal material.

According to embodiments of the disclosure, suitable material of the separator 14 can be glass fiber, polyethylene (PE), polypropylene (PP), non-woven fabric, wood fiber, poly(ether sulfone) (PES), ceramic fiber, or a combination thereof.

According to embodiments of the disclosure, the negative electrode 12 includes an active material of the negative electrode, wherein the active material of the negative electrode can be a metal or an alloy of the metal, layered carbon material, layered double hydroxide, layered oxide, layered chalcogenide, vanadium oxide, metal sulfide, a combination thereof. According to embodiments of the disclosure, the metal can be aluminum, copper, iron, indium, nickel, tin, chromium, yttrium, titanium, manganese, or molybdenum. According to embodiments of the disclosure, the layered carbon material can be graphite, carbon nanotube, graphene, or a combination thereof. According to embodiments of the disclosure, the layered carbon material can be intercalated carbon material, such as graphite (e.g., natural graphite, electrographite, pyrolytic graphite, foamed graphite, flake graphite, or expanded graphite), graphene, carbon nanotube, or a combination thereof. According to embodiments of the disclosure, the negative electrode 12 can further include a current-collecting layer of the negative electrode, and the active material of the negative electrode can grow directly (i.e. there is no other layer between the active material and the current-collecting layer) on the current-collecting layer of the negative electrode. For example, the active material can grow directly on the current-collecting layer by chemical vapor deposition (CVD). Furthermore, the active material of the negative electrode can be affixed to the current-collecting layer of the negative electrode via an adhesive. The adhesive can be polyvinyl alcohol (PVA), polytetrafluoroethylene (PTFE), carboxymethyl cellulose sodium, polyvinylidene difluoride (PVDF), styrene-butadiene copolymer, fluorinated rubber, polyurethane, polyvinylpyrrolidone, poly(ethyl acrylate), polyvinyl chloride, polyacrylonitrile, polybutadiene, polyacrylic acid, or a combination thereof. According to embodiments of the disclosure, the current-collecting layer of the negative electrode can be a conductive carbon substrate, such as carbon cloth, carbon felt, or carbon paper. For example, the conductive carbon substrate can have a sheet resistance from about 1 $m\Omega \cdot cm^2$ to 6 $m\Omega \cdot cm^2$, and the carbon content of the conductive carbon substrate is greater than about 65 wt %. According to embodiments of the disclosure, the current-collecting layer of the negative electrode can be a metal material with porous structure, such as metal material having a three-dimensional network structure (such as nickel net, copper net, or molybdenum net) or metal material having a foam structure (such as nickel foam, copper foam, or molybdenum foam). According to embodiments of the disclosure, a metal material with porous structure can have a porosity P from about 50% to 80% (such as about 60%, or 70%). The porosity P can be determined by the following equation: $P=V1/V2\times 100\%$, wherein V1 is the volume of the pores of the current-collecting layer of the negative electrode, and V2 is the volume of the current-collecting layer of the negative electrode. According to embodiments of the disclosure, the current-collecting layer of the negative electrode can be a composite layer of the conductive carbon substrate and a metal material. According to embodiments of the disclosure, when the current-collecting layer of the negative electrode is metal material with porous structure, the active material of the negative electrode can further fill into the pores of the metal material. According to embodiments of the disclosure, the negative electrode can consist of the current-collecting layer of the negative electrode and the active material of the negative electrode. According to embodiments of the disclosure, the material of the positive electrode 10 and the negative electrode 12 is the same, and the structure of the positive electrode 10 and the negative electrode 12 is the same.

Below, exemplary embodiments will be described in detail with reference to the accompanying drawings so as to

EXAMPLES

Preparation of Electrolyte Composition

Example 1

Aluminum chloride and 1,2-dimethyl-3-propylimidazolium chloride (DMPIC) were mixed, wherein the molar ratio of aluminum chloride to 1,2-dimethyl-3-propylimidazolium chloride (DMPIC) was 1.1. Next, lithium chloride was added into the result, wherein lithium chloride had a weight percentage of 5.2 wt %, based on the total weight of aluminum chloride and 1,2-dimethyl-3-propylimidazolium chloride (DMPIC). After stirring for 12 hours, lithium bis(oxalato)borate (LiBOB) was added into the result, wherein lithium bis(oxalato)borate (LiBOB) had a molar percentage of 1 mol %, based on the total moles of the aluminum chloride and the 1,2-dimethyl-3-propylimidazolium chloride (DMPIC). After stirring for 12 hours, Electrolyte composition (1) was obtained.

Example 2

Example 2 was performed in the same manner as Example 1 except that the molar percentage of lithium bis(oxalato)borate (LiBOB) was reduced from 1 mol % to 0.5 mol %, obtaining Electrolyte composition (2).

Example 3

Example 3 was performed in the same manner as Example 1 except that the molar percentage of lithium bis(oxalato)borate (LiBOB) was increased from 1 mol % to 1.5 mol %, obtaining Electrolyte composition (3).

Example 4

Example 4 was performed in the same manner as Example 1 except that the molar percentage of lithium bis(oxalato)borate (LiBOB) was increased from 1 mol % to 2 mol %, obtaining Electrolyte composition (4).

Comparative Example 1

Comparative Example 1 was performed in the same manner as Example 1 except that the molar ratio of aluminum chloride to 1,2-dimethyl-3-propylimidazolium chloride (DMPIC) was reduced from 1.1 to 0.95, obtaining Electrolyte composition (5).

Comparative Example 2

Comparative Example 2 was performed in the same manner as Example 1 except that the molar ratio of aluminum chloride to 1,2-dimethyl-3-propylimidazolium chloride (DMPIC) was reduced from 1.1 to 1, obtaining Electrolyte composition (6).

Comparative Example 3

Comparative Example 3 was performed in the same manner as Example 1 except that lithium bis(oxalato)borate (LiBOB) was not added, obtaining Electrolyte composition (7).

Comparative Example 4

Comparative Example 4 was performed in the same manner as Example 1 except that 1,2-dimethyl-3-propylimidazolium chloride (DMPIC) was replaced with 1-ethyl-3-methylimidazolium chloride (EMIC), obtaining Electrolyte composition (8).

Comparative Example 5

Comparative Example 5 was performed in the same manner as Example 1 except that 1,2-dimethyl-3-propylimidazolium chloride (DMPIC) was replaced with 1-butyl-3-methylimidazolium chloride (BMIC), obtaining Electrolyte composition (9).

Comparative Example 6

Comparative Example 6 was performed in the same manner as Example 1 except that lithium chloride was not added, obtaining Electrolyte composition (10).

Comparative Example 7

Comparative Example 7 was performed in the same manner as Example 1 except that lithium bis(oxalato)borate (LiBOB) was replaced with ethylene sulfite (ES), obtaining Electrolyte composition (11).

Comparative Example 8

Comparative Example 8 was performed in the same manner as Example 1 except that lithium bis(oxalato)borate (LiBOB) was replaced with fluoroethylene carbonate (FEC), obtaining Electrolyte composition (12).

Example 5

Example 5 was performed in the same manner as Example 1 except that weight percentage of lithium chloride was reduced from 5.2 wt % to 1.3 wt %, obtaining Electrolyte composition (13).

Metal-Ion Battery

Example 6

First, a nickel foam sheet (having a size of 100 mm×100 mm, a thickness of 0.2 mm, a porosity of 90%, and a pore diameter of 200 μm) was provided. Next, the nickel foam sheet was disposed in a vacuum muffle furnace, and then hydrogen gas, argon gas (serving as carrier gas), and methane gas were introduced into the vacuum muffle furnace to perform a graphite vapor deposition (at a temperature of 900° C. to 1100° C.), obtaining a graphite electrode (nickel foam sheet with a graphite layer covering the surface thereof) with a graphite loading amount of about 800-1500 mg. Next, a separator (six layers of ½ inch glass filter paper, with trade No. Whatman 934-AH) was provided. Next, the graphite electrode (serving as negative electrode), the separator, and the graphite electrode (serving as positive electrode) were placed in sequence and sealed within an aluminum plastic pouch. Next, Electrolyte composition (1) was injected into the aluminum plastic pouch, obtaining Metal-ion battery (1).

Next, Metal-ion battery (1) was activated with a current of 80 mAg$^{-1}$. After the activating process, Metal-ion battery (1) was subjected to a charge-discharge testing (charged to about 4.2 V) with a current of 500 mAg$^{-1}$. The discharging mean voltage and power density of Metal-ion battery (1) on the 9$^{th}$ charging/discharging cycle were measured. Furthermore, the life cycle (determined by the equation: power density/maximum power density×100%) of Metal-ion battery (1) on the 15$^{th}$ charging/discharging cycle was measured. The results are shown in Table 1.

Examples 7-9

Examples 7-9 were performed in the same manner as Example 6 except that Electrolyte composition (1) was replaced with Electrolyte compositions (2)-(4) individually, obtaining Metal-ion batteries (2)-(4).

Next, according to above mentioned method, the discharging mean voltage and power density of Metal-ion batteries (2)-(4) on the 9$^{th}$ charging/discharging cycle were measured. Furthermore, the life cycle (determined by the equation: power density/maximum power density×100%) of Metal-ion batteries (2)-(4) on the 15$^{th}$ charging/discharging cycle was measured. The results are shown in Table 1.

Comparative Example 9-16

Comparative Examples 9-16 were performed in the same manner as Example 6 except that Electrolyte composition (1) was replaced with Electrolyte compositions (5)-(12) individually, obtaining Metal-ion batteries (5)-(12).

Next, according to above mentioned method, the discharging mean voltage and power density of Metal-ion batteries (5)-(12) on the 9$^{th}$ charging/discharging cycle were measured. Furthermore, the life cycle (determined by the equation: power density/maximum power density×100%) of Metal-ion batteries (5)-(12) on the 15$^{th}$ charging/discharging cycle was measured. The results are shown in Table 1.

Example 10

Example 10 was performed in the same manner as Example 6 except that Electrolyte composition (1) was replaced with Electrolyte composition (13), obtaining Metal-ion battery (13).

Next, according to above mentioned method, the discharging mean voltage and power density of Metal-ion battery (13) on the 9$^{th}$ charging/discharging cycle were measured. Furthermore, the life cycle (determined by the equation: power density/maximum power density×100%) of Metal-ion battery (13) on the 15$^{th}$ charging/discharging cycle was measured. The results are shown in Table 1.

TABLE 1

| | imidazolium salt | additive | molar ratio of aluminum chloride to imidazolium salt | lithium chloride (wt %) | additive (mol %) | discharging mean voltage (V) | power density (mWh/g) | life cycle (%) |
|---|---|---|---|---|---|---|---|---|
| Example 6 | DMPIC | LiBOB | 1.1 | 5.2 wt % | 1 mol % | 3.29 | 178.1 | 100.0% |
| Example 7 | DMPIC | LiBOB | 1.1 | 5.2 wt % | 0.5 mol % | 3.26 | 167.7 | 85.4% |
| Example 8 | DMPIC | LiBOB | 1.1 | 5.2 wt % | 1.5 mol % | 3.32 | 163.2 | 95.5% |
| Example 9 | DMPIC | LiBOB | 1.1 | 5.2 wt % | 2 mol % | 3.12 | 74.2 | 98.0% |
| Comparative Example 9 | DMPIC | LiBOB | 0.95 | 5.2 wt % | 1 mol % | 2.01 | 31.3 | 25.5% |
| Comparative Example 10 | DMPIC | LiBOB | 1 | 5.2 wt % | 1 mol % | 3.03 | 115.9 | 63.9% |
| Comparative Example 11 | DMPIC | LiBOB | 1.1 | 5.2 wt % | 0 | 3.30 | 156.1 | 89.0% |
| Comparative Example 12 | EMIC | LiBOB | 1.1 | 5.2 wt % | 1 mol % | 2.04 | 153.9 | 91.9% |
| Comparative Example 13 | BMIC | LiBOB | 1.1 | 5.2 wt % | 1 mol % | 1.54 | 29.3 | 87.4% |
| Comparative Example 14 | DMPIC | LiBOB | 1.1 | 0 | 1 mol % | 2.29 | 116.4 | 98.4% |
| Comparative Example 15 | DMPIC | ES | 1.1 | 5.2 wt % | 1 mol % | 3.17 | 22.9 | 100% |
| Comparative Example 16 | DMPIC | FEC | 1.1 | 5.2 wt % | 1 mol % | 3.49 | 104.3 | 92.4% |
| Example 10 | DMPIC | LiBOB | 1.1 | 1.3 wt % | 1 mol % | 3.13 | 87.1 | 93.8% |

As shown in Table 1, since the molar ratio of metal chloride to imidazolium salt of the electrolyte compositions disclosed in Comparative Examples 9 and 10 is less than 1.05, the operating voltage (discharging mean voltage is less than 3.1V) and life cycle (lower than 70%) of the metal-ion batteries disclosed in Comparative Examples 9 and 10 are inferior than those of metal-ion batteries disclosed in Examples 6-10, even though the electrolyte compositions of disclosed in Comparative Example 9 and Comparative Example 10 employ the alkali halide and oxalate-containing borate of the disclosure. Since the electrolyte composition disclosed in Comparative Example 11 does not employ the oxalate-containing borate of the disclosure, the power density (less than 160 mWh/g) of the metal-ion battery disclosed in Comparative Example 11 is inferior than that of the metal-ion batteries disclosed in Examples 6-8. In Comparative Examples 12 and 13, since EMIC (or BMIC) replaces the imidazolium salt having a structure represented by Formula (I), the operating voltage (discharging mean voltage is less than 2.1V) of the metal-ion batteries disclosed in Comparative Examples 12 and 13 is inferior than that of the metal-ion batteries disclosed in Examples 6-10. Since the electrolyte composition disclosed in Comparative Example 14 does not employ the alkali halide of the disclosure, the operating voltage (discharging mean voltage is less than 2.3V) of the metal-ion battery disclosed in Comparative Example 14 is inferior than that of the metal-ion batteries disclosed in Examples 6-10. In Comparative Examples 15 and 16, since ES (or FEC) replaces the oxalate-containing borate of the disclosure, the power density (less than 105 mWh/g) of the metal-ion batteries disclosed in Comparative Examples 15 and 16 is inferior than the power density (greater than 163 mWh/g) of the metal-ion batteries disclosed in Examples 6-10.

It will be clear that various modifications and variations can be made to the disclosed methods and materials. It is intended that the specification and examples be considered as exemplary only, with the true scope of the disclosure being indicated by the following claims and their equivalents.

What is claimed is:

1. An electrolyte composition, comprising:
a metal chloride, wherein the metal chloride is aluminum chloride, ferric chloride, zinc chloride, cupric chloride, manganese chloride, chromium chloride, or a combination thereof;
an imidazolium salt having a structure represented by Formula (I)

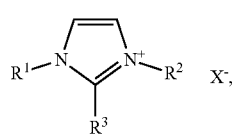

Formula (I)

wherein $R^1$, $R^2$, $R^3$ are independently $C_{1-8}$ alkyl, $C_{2-8}$ alkenyl, $C_{2-8}$ alkynyl, $C_{1-8}$ alkoxy group, $C_{2-8}$ alkoxyalkyl, or $C_{1-8}$ fluoroalkyl; and, $X^-$ is $F^-$, $Cl^-$, $Br^-$, or $I^-$;
an alkali halide; and
an oxalate-containing borate.

2. The electrolyte composition as claimed in claim 1, wherein a molar ratio of the metal chloride to the imidazolium salt is from 1.05 to 1.2.

3. The electrolyte composition as claimed in claim 1, wherein the imidazolium salt is

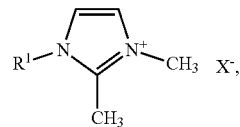

wherein $R^1$ is $C_{1-8}$ alkyl, $C_{2-8}$ alkenyl, $C_{2-8}$ alkynyl, $C_{1-8}$ alkoxy, $C_{2-8}$ alkoxyalkyl, or $C_{1-8}$ fluoroalkyl; and, $X^-$ is $F^-$, $Cl^-$, $Br^-$, or $I^-$.

4. The electrolyte composition as claimed in claim 3, wherein the imidazolium salt is 1,2-dimethyl-3-propylimidazolium chloride (DMPIC), 1,2-dimethyl-3-propylimidazolium iodide, 1,2-dimethyl-3-propylimidazolium bromide, 1,2-dimethyl-3-propylimidazolium fluoride, 1,2-dimethyl-3-butylimidazolium chloride (DMBIC), 1,2-dimethyl-3-butylimidazolium iodide, 1,2-dimethyl-3-butylimidazolium bromide, 1,2-dimethyl-3-butylimidazolium fluoride, 1,2-dimethyl-3-ethylimidazolium chloride (DMEIC), 1,2-dimethyl-3-ethylimidazolium iodide, 1,2-dimethyl-3-ethylimidazolium bromide, 1,2-dimethyl-3-ethylimidazolium fluoride, or a combination thereof.

5. The electrolyte composition as claimed in claim 1, wherein the alkali halide is lithium chloride, sodium chloride, potassium chloride, rubidium chloride, cesium chloride, lithium fluoride, sodium fluoride, potassium fluoride, rubidium fluoride, cesium fluoride, lithium fluoride, sodium bromide, potassium bromide, rubidium bromide, cesium bromide, lithium iodide, sodium iodide, potassium iodide, rubidium iodide, cesium iodide, or a combination thereof.

6. The electrolyte composition as claimed in claim 1, wherein a ratio of a weight of the alkali halide to a total weight of the metal chloride and the imidazolium salt is from 1:100 to 6:100.

7. The electrolyte composition as claimed in claim 1, wherein the oxalate-containing borate is

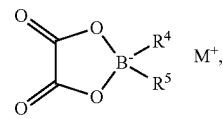

wherein $R^4$ and $R^5$ is halogen, or $R^4$ and $R^5$ form an oxalate ligand

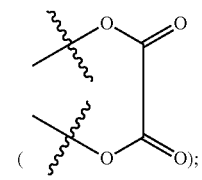

and, $M^+$ is $Li^+$ or $Na^+$.

8. The electrolyte composition as claimed in claim 1, wherein the oxalate-containing borate is lithium bis(oxalato)borate (LiBOB), sodium bis(oxalato)borate (NaBOB), lithium difluoro(oxalato)borate (LiODFB), sodium difluoro(oxalato)borate (NaODFB), or a combination thereof.

9. The electrolyte composition as claimed in claim 1, wherein a ratio of a molar amount of the oxalate-containing borate to a total molar amount of the metal chloride and the imidazolium salt is from 0.1:100 to 2:100.

10. A metal-ion battery, comprising:
a positive electrode;
a separator;
a negative electrode, wherein the negative electrode and the positive electrode are separated by the separator; and
the electrolyte composition as claimed in claim 1, wherein the electrolyte composition is disposed between the positive electrode and the negative electrode.

11. The metal-ion battery as claimed in claim 10, wherein the positive electrode consists of a current-collecting layer of the positive electrode and an active material of the positive electrode.

12. The metal-ion battery as claimed in claim 11, wherein the current-collecting layer of the positive electrode is a conductive carbon substrate, a metal material with porous structure, or a combination thereof.

13. The metal-ion battery as claimed in claim 11, wherein the active material of the positive electrode is layered carbon material, layered double hydroxide, layered oxide, layered chalcogenide, vanadium oxide, or metal sulfide.

14. The metal-ion battery as claimed in claim 13, wherein layered carbon material is natural graphite, electrographite, pyrolytic graphite, foamed graphite, flake graphite, expanded graphite, graphene, carbon nanotube, or a combination thereof.

15. The metal-ion battery as claimed in claim 10, wherein the negative electrode comprises an active material of the negative electrode.

16. The metal-ion battery as claimed in claim 15, wherein the active material of the negative electrode is a metal, an alloy of the metal, layered carbon material, layered double hydroxide, layered oxide, layered chalcogenide, vanadium oxide, or metal sulfide.

17. The metal-ion battery as claimed in claim 16, wherein the metal is copper, iron, aluminum, zinc, indium, nickel, tin, chromium, yttrium, titanium, manganese, or molybdenum.

18. The metal-ion battery as claimed in claim 16, wherein layered carbon material is natural graphite, electrographite, pyrolytic graphite, foamed graphite, flake graphite, expanded graphite, graphene, carbon nanotube, or a combination thereof.

19. The metal-ion battery as claimed in claim 15, wherein the negative electrode further comprises a current-collecting layer of the negative electrode, the current-collecting layer of the negative electrode is conductive carbon substrate, nickel mesh, nickel foam, molybdenum mesh, molybdenum foam, or a combination thereof.

20. The metal-ion battery as claimed in claim 10, the separator is glass fiber, polyethylene, polypropylene, non-woven fabric, wood fiber, poly(ether sulfones), ceramic fiber, or a combination thereof.

* * * * *